US008419916B2

(12) United States Patent
Sakairi et al.

(10) Patent No.: US 8,419,916 B2
(45) Date of Patent: Apr. 16, 2013

(54) BIOLOGICAL MOLECULE SEPARATION APPARATUS

(75) Inventors: Koji Sakairi, Tokyo (JP); Satonari Akutsu, Tokyo (JP); Atsunori Hiratsuka, Tokyo (JP); Kenji Yokoyama, Tokyo (JP); Yuji Maruo, Osaka (JP); Hiroshi Ohki, Osaka (JP)

(73) Assignee: Toppan Printing Co., Ltd. (JP)

( * ) Notice: Subject to any disclaimer, the term of this patent is extended or adjusted under 35 U.S.C. 154(b) by 155 days.

(21) Appl. No.: 13/073,835

(22) Filed: Mar. 28, 2011

(65) Prior Publication Data

US 2011/0233062 A1    Sep. 29, 2011

Related U.S. Application Data

(63) Continuation of application No. PCT/JP2009/067816, filed on Oct. 14, 2009.

(30) Foreign Application Priority Data

Oct. 15, 2008   (JP) ................................ 2008-266759

(51) Int. Cl.
*G01N 27/26*   (2006.01)
(52) U.S. Cl.
USPC ........................................ 204/627; 204/629
(58) Field of Classification Search .................. 204/627, 204/629
See application file for complete search history.

(56) References Cited

U.S. PATENT DOCUMENTS

| 4,889,606 A | 12/1989 | Dyson et al. |
| 2006/0042951 A1 | 3/2006 | Ohse et al. |
| 2007/0045118 A1 | 3/2007 | Maruo et al. |
| 2008/0296158 A1* | 12/2008 | Maruo et al. .................. 204/600 |

FOREIGN PATENT DOCUMENTS

| JP | 2001544 | 1/1990 |
| JP | 2000-028578 | 1/2000 |
| JP | 2006-071494 | 3/2006 |
| JP | 2007-064848 | 3/2007 |

OTHER PUBLICATIONS

Translation of Notification of Reasons for Refusal for JP appl. 2008-266759, mailed Mar. 6, 2012, 3 pgs.

* cited by examiner

*Primary Examiner* — Arun S Phasge
(74) *Attorney, Agent, or Firm* — Squire Sanders (US) LLP (57) ABSTRACT

A biological molecule separation apparatus for separating a biological molecule of one embodiment of the present invention has a buffer solution chamber receiving a buffer solution, a separation electrode arranged in the buffer solution chamber, a biological molecule separation medium for separating a biological molecule, a biological molecule adsorption film for adsorbing a biological molecule, a pair of transfer electrodes having a plurality of line shaped conductors extending in a direction perpendicular to a first direction, the conductors being arranged in the direction perpendicular to the first direction, and a separation part which holds the transfer electrode, the biological molecule adsorption film, the medium and the transfer electrode, wherein the transfer electrode, the biological molecule adsorption film, the medium and the transfer electrode are stacked in this order.

6 Claims, 6 Drawing Sheets

| Only electrophoresis was performed. (a separation pattern in a gel) | Electrophoresis and transfer were continuously performe. |
|---|---|
|   First time | A gel after transfer |
|  Second time |  A transfer film |

Fig. 6

BIOLOGICAL MOLECULE SEPARATION APPARATUS

CROSS REFERENCE TO RELATED APPLICATION

This application is a continuation of PCT International Application No. PCT/JP2009/067816, filed Oct. 14, 2009 the entire disclosure of which is incorporated herein by reference.

BACKGROUND OF THE INVENTION

1. Field of the Invention

The present invention is related to an apparatus for separating a biological molecule, the apparatus using electrophoresis.

2. Description of the Related Art

In proteome analysis, one dimension electrophoresis, two dimension electrophoresis and transfer of a sample to a film are continuously performed. A technology in which these steps are simplified is needed.

Patent document 1 discloses an apparatus which automates one dimension electrophoresis and two dimension electrophoresis.

Patent document 2 discloses a biological molecule separation apparatus in which both electrophoresis and transfer are performed.

However, in the apparatus described in the patent document 2, it is necessary that a gel is once peeled after electrophoresis. Therefore, a troublesome operation requiring a lot of skill is necessary.

Patent document 3 proposes a biological molecule separation apparatus in which peeling of a gel is not needed and both electrophoresis and transfer are performed by a simple operation.

patent document 1: JP-A-2007-64848
patent document 2: JP-A-2000-28578
patent document 3: JP-A-2006-71494

However, a practical biological molecule separation apparatus in which both electrophoresis and transfer can be performed by a simple operation does not yet exist.

As mentioned above, in the apparatus described in the patent document 2, an operation requiring a lot of skill or a troublesome operation is needed. In addition, according to study by the inventors of the present invention, it was very difficult to perform electrophoresis in an apparatus having a structure in which a transfer electrode is simply arranged at a path of electrophoresis, as the apparatus described in the patent document 3. In particular, in the biological molecule separation apparatus having the above structure in which both electrophoresis and transfer are performed, during electrophoresis, a voltage could not be applied and thereby a sample could not be moved.

The present invention was made by considering the above problem. An object of the present invention is to provide a practical biological molecule separation apparatus in which both electrophoresis and transfer are performed by a simple operation.

SUMMARY OF THE INVENTION

A biological molecule separation apparatus related to the present invention is as follows in order to solve the problem. A biological molecule separation apparatus, having a first separation electrode, a second separation electrode, a first buffer solution chamber, the first separation electrode arranged in the first buffer solution chamber, and the first buffer solution chamber receiving a buffer solution, a second buffer solution chamber, the second separation electrode arranged in the second buffer solution chamber, and the second buffer solution chamber receiving a buffer solution, a biological molecule separation medium, one end of the medium exposed on the first buffer solution chamber, and the other end of the medium exposed on the second buffer solution chamber, a biological molecule adsorption film, a first transfer electrode comprising a first plurality of line-shaped conductors extending in a direction perpendicular to a first direction, the first direction defined by the first buffer solution chamber and the second buffer solution chamber, and the conductors arranged in the first direction, a second transfer electrode comprising a second plurality of line-shaped conductors extending in a direction perpendicular to the first direction, and the conductors arranged in the first direction, and a holding part which holds the first transfer electrode, the biological molecule adsorption film, the medium and the second transfer electrode, wherein the first transfer electrode, the biological molecule adsorption film, the medium and the second transfer electrode are stacked in this order.

According to the above structure, the following is performed. The first separation electrode and the second separation electrode separate a biological molecule in the medium. Thereafter, the biological molecule can be transferred from the medium to the biological molecule adsorption film, using the first transfer electrode and the second transfer electrode sandwiching both the medium and the biological molecule adsorption film formed on the medium.

Here, the first transfer electrode has a plurality of line-shaped conductors extending in a direction perpendicular to a first direction, the first direction defined by the first buffer solution chamber and the second buffer solution chamber, and the conductors arranged in the first direction, and the second transfer electrode has a plurality of line-shaped conductors extending in a direction perpendicular to the first direction, and the conductors arranged in the first direction. Even if the first transfer electrode and the second transfer electrode exist, the first transfer electrode and the second transfer electrode do not prevent a voltage by the first separation electrode and the second separation electrode from being applied. Therefore, separation and transfer of a biological molecule can be continuously performed just by operating the state of an electric current flowing through the separation electrode and the transfer electrode.

As mentioned above, according to the above structure, a practical biological molecule separation apparatus in which an operation requiring a lot of skill and a troublesome operation are not needed, the apparatus being able to perform both electrophoresis and transfer, can be provided.

It is preferable that the biological molecule separation apparatus further has a first substrate on which the first transfer electrode is arranged and a second substrate on which the second transfer electrode is arranged, wherein the holding part holds the first substrate and the second substrate.

According to the above structure, the following (A) and (B) are individually formed. (A) The first substrate on which the first transfer electrode is arranged, and the second substrate on which the second transfer electrode is arranged, and (B) the holding part. The holding part holds the first substrate and the second substrate. Therefore, after, for example, several kinds of the first substrates and the second substrates are manufactured. The biological molecule separation apparatus can be manufactured by appropriately selecting the first substrate and the second substrate. Accordingly, a biological molecule separation apparatus can be easily manufactured, the apparatus having a suitable transfer electrode.

In the biological molecule separation apparatus, it is preferable that the first substrate and the second substrate are made of a resin or a paper.

According to the above structure, the first substrate and the second substrate can be made porous. A porous substance can be arranged near the first transfer electrode and the second transfer electrode. Bubbles due to electrolysis of water are generated from the above electrodes. The bubbles influence transfer. However, in the case of the above structure, the bubbles generated at the electrodes are adsorbed on the porous substance, and the bubbles can be easily removed.

In the biological molecule separation apparatus, the first transfer electrode and the second transfer electrode may be formed on the holding part.

In the case of the above structure, the number of components of the biological molecule separation apparatus is small. Therefore, the manufacturing process can be simplified.

In the biological molecule separation apparatus, it is preferable that one end of the first transfer electrode in the direction perpendicular to the first direction and one end of the second transfer electrode in the direction perpendicular to the first direction, the one end of the second transfer electrode being opposite to the one end of the first transfer electrode, are exposed on the holding part.

In the above structure, an end part of the first transfer electrode and an end part of the second transfer electrode are alternately exposed. Therefore, if a conductor which contacts with all of the end part is prepared, wire connection can be easily performed, thereby a voltage can be applied. In this way, even if a transfer electrode has a unique structure which is comprised of a plurality of line shaped conductors extending in a direction perpendicular to a first direction, the conductors being arranged along the first direction, conductor connection can be easily performed.

The above biological molecule separation apparatus further preferably has a porous film between the first transfer electrode and the biological molecule adsorption film and a porous film between the biological molecule separation medium and the second transfer electrode, one side of the porous film exposed to the first buffer solution tank and another side of the porous film exposed to the second buffer solution tank.

According to the above structure, the buffer solution received in the first buffer solution tank or the second buffer solution tank penetrates the porous film. Therefore, drying of the biological molecule separation medium can be prevented. At the same time, bubbles generated at the first transfer electrode and the second transfer electrode are adsorbed by the porous film and thereby the bubbles can be removed.

A first aspect of the present invention is a biological molecule separation apparatus, including:
a first separation electrode;
a second separation electrode;
a first buffer solution chamber, the first separation electrode arranged in the first buffer solution chamber, and the first buffer solution chamber receiving a buffer solution;
a second buffer solution chamber, the second separation electrode arranged in the second buffer solution chamber, and the second buffer solution chamber receiving a buffer solution;
a biological molecule separation medium, one end of the biological molecule separation medium exposed on the first buffer solution chamber, and the other end of the biological molecule separation medium exposed on the second buffer solution chamber;
a biological molecule adsorption film;
a first transfer electrode including a first plurality of line-shaped conductors extending in a direction perpendicular to a first direction, the first direction defined by the first buffer solution chamber and the second buffer solution chamber, the first plurality of line-shaped conductors being arranged in the first direction;
a second transfer electrode including a second plurality of line-shaped conductors extending in a direction perpendicular to the first direction, the second plurality of line-shaped conductors being arranged in the first direction; and,
a holding part which holds the first transfer electrode, the biological molecule adsorption film, the biological molecule separation medium and the second transfer electrode, wherein the first transfer electrode, the biological molecule adsorption film, the biological molecule separation medium and the second transfer electrode are stacked in this order.

A second aspect of the present invention is the apparatus according to the first aspect, further including:
a first substrate on which the first transfer electrode is arranged; and
a second substrate on which the second transfer electrode is arranged,
wherein
the holding part holds the first substrate and the second substrate.

A third aspect of the present invention is the apparatus according to the second aspect, wherein the first substrate and the second substrate are made of a resin or a paper.

A fourth aspect of the present invention is the apparatus according to the first aspect, wherein the first transfer electrode and the second transfer electrode are formed on the holding part.

A fifth aspect of the present invention is the apparatus according to the first aspect, wherein one end of the first transfer electrode and one end of the second transfer electrode are exposed on the holding part, and the one end of the second transfer electrode is opposite to the one end of the first transfer electrode.

A sixth aspect of the present invention is the apparatus according to the first aspect, further including:
a first porous film arranged between the first transfer electrode and the biological molecule adsorption film and a second porous film arranged between the biological molecule separation medium and the second transfer electrode;
wherein
one side of the first porous film is exposed on the first buffer solution chamber and the other side of the first porous film is exposed on the second buffer solution chamber,
and
one side of the second porous film is exposed on the first buffer solution chamber and the other side of the second porous film is exposed on the second buffer solution chamber.

100 . . . a biological molecule separation apparatus
101 . . . a separation electrode (a first separation electrode)
102 . . . a separation electrode (a second separation electrode)
103 . . . a buffer solution chamber (a first buffer solution chamber)
104 . . . a buffer solution chamber (a second buffer solution chamber)
105 . . . a separation part (a holding part)
110 . . . a transfer electrode (a first transfer electrode)
111 . . . a transfer electrode (a second transfer electrode)
115 . . . a substrate (a first substrate)
116 . . . a substrate (a second substrate)
122 . . . a biological molecule adsorption film
125 . . . a biological molecule separation medium
120 and 121 . . . a porous film
160 . . . a buffer solution

DETAILED DESCRIPTION OF THE INVENTION

Figure 1:
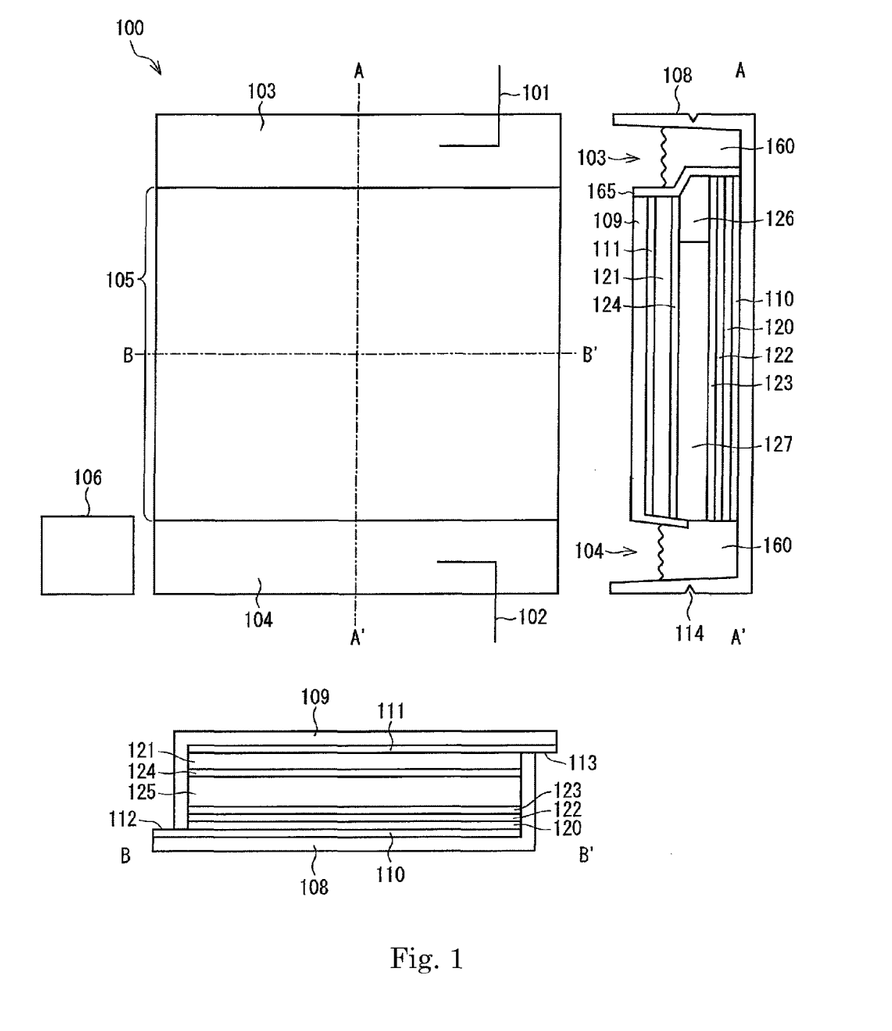
FIG. 1 is a schematic diagram showing a structure of a biological molecule separation apparatus related to one embodiment of the present invention.

FIG. 1 is a schematic diagram showing a structure of a biological molecule separation apparatus 100 related to one embodiment of the present invention. Hereinafter, the structure of the biological molecule separation apparatus 100 is explained using FIG. 1.

[Schematic Structure]

The biological molecule apparatus 100 has a buffer solution chamber 103 in which a separation electrode 101 is arranged, a buffer solution chamber 104 in which a separation electrode 102 is arranged, a separation part (a holding part) between the buffer solution chamber 103 and the buffer solution chamber 104, and a power source 106. In addition, in the above structure, a part including the buffer solution chamber 103, the buffer solution chamber 104 and the separation part 105 may be called a biological molecule separation structure (chip) 107.

As shown in FIG. 1, the separation part 105 has a separation part housing 108, a porous film 120, a biological molecule adsorption film 122, a peeling film 123, a biological molecule separation medium 125, a peeling film 124, a porous film 121 and a separation part housing 109. A structure is formed in which these components are stacked in that order in a second direction perpendicular to a first direction, the first direction defined by the buffer solution chamber 103 and the buffer solution chamber 104 (from the buffer solution chamber 103 to the buffer solution chamber 104, or, from the buffer solution chamber 104 to the buffer solution chamber 103). In addition, parts comprised of the biological molecule adsorption film 122, a peeling film 123, a biological molecule separation medium 125 and a peeling film 125, in the structure, may be called a separation part stacked body 129.

Transfer electrodes 110 and 111 are respectively arranged in surfaces of separation part housings 108 and 109, the surfaces arranged to face each other, and each of the surfaces contacts with the porous film 120 or 121. As shown in FIG. 1, one end 112 of the transfer electrode 110 and one end 113 of the transfer electrode 111 are alternately exposed on the separation part housings 108 and 109.

The biological molecule separation medium 125 is comprised of two parts which are divided in the first direction. That is, one part is a first step separation medium 126 in a side of the buffer solution tank 103 (a side of the separation electrode 101). Another part is in a side of a second step separation medium 127 in a side of the buffer solution tank 104 (a side of the separation electrode 102).

In addition, both ends of the porous film 120, the biological molecule separation medium 125 and the porous film 121 in the first direction are respectively exposed to the buffer solution tanks 103 and 104. In addition, in FIG. 1, a cover 165 for manufacturing the first step separation medium 126 covers the biological molecule separation medium 125. However, in the case where the biological molecule separation apparatus 100 is operated, the cover 165 is removed.

[Outline of Operation]

A biological molecule separation apparatus 100 is operated as follows. Firstly, for preparation, the buffer solution chamber 103 and the buffer solution chamber 104 are filled with a buffer solution 160. A sample including a biological molecule to be separated is introduced into a first step separation medium 126. Thereafter, the power source is electrically connected to the separation electrode 101 and the separation electrode 102 and thereby a separation process is performed.

In addition, in the case where the biological molecule separation apparatus 100 is used for a two dimension electrophoresis, as a sample including a biological molecule, a long and thin gel or the like in a state where a biological molecule is separated by one dimension electrophoresis is used. Introduction of a sample into the first step separation medium 126 can be performed by contacting a sample of a gel with a surface of the first step separation medium 126.

In addition, in another embodiment, a solution including a biological molecule is used as a sample, and a hole used for injecting the sample is provided at the first step separation medium 126. Thereby, the introduction of the sample into the first step separation medium 126 may be performed by injecting the sample into the hole.

A biological molecule to be separated can be taken into the first step separation medium 126 by any means.

In the separation process, a voltage is applied between the separation electrode 101 and the separation electrode 102. Thereby, electrophoresis of a biological molecule inside the biological separation medium 125 is performed. At this time, a second step separation medium 127 of the biological molecule separation medium 125 functions as a molecular sieve. The above biological molecule is separated based on the difference of its molecular weight.

Detailed descriptions are as follows. The separation process includes a first step (a condensation step) and a second step (a separation step). In the first step, a biological molecule taken into the first step separation medium 126 remains inside the first step separation medium 126. At this time, an effect of a molecular sieve of the first step separation medium 126 is much smaller than that of the second step separation medium 127. Therefore, the above biological molecule moves faster inside the first step separation medium 126 than inside the second step separation medium. Therefore, the above biological molecule is once condensed at an interface between the first step separation medium 126 and the second step separation medium. Thereby, an error due to position or the like of a biological molecule in the sample can be prevented. Thereafter, the biological molecule condensed at the interface is separated in the second step separation medium 127.

Next, the electrical connection of the power source 106 with the separation electrode 101 and the separation electrode 102 is cut. Instead, the power source 106 is electrically connected with respective ends 112 and 113 of the transfer electrodes 110 and 111. Thereby, a transfer process is performed.

In the transfer process, a voltage is applied between the transfer electrodes 101 and 102. Thereby, a biological molecule inside the biological molecule separation medium 125 is electrophoresed toward the biological molecule adsorption film 122. Thereby, the biological molecule is transferred to the biological molecule adsorption film 122.

In this way, the biological molecule adsorption film 122 on which a separated biological molecule is adsorbed can be obtained. For example, in a recovery process, the separation part housings 108 and 109 are peeled from each other. Thereby, the biological molecule adsorption film 122 is recovered. The recovered biological molecule adsorption film 122 is analyzed in a subsequent process. (fluorescence reaction, immune reaction or the like)

[Detailed Descriptions of Respective Components]

As long as the buffer solution chambers 103 and 104, and, separation part housings 108 and 109 are formed of an insulating body, its material or the like is not specially limited.

As long as the buffer solution chambers 103 and 104 hold the buffer solution 160 without leaking and have a structure in which separation electrodes 101 and 102 are arranged so as to contact with the buffer solution 160, any buffer solution chambers can be used. For example, typically, the buffer solution chambers 103 and 104 can have a shape with a square outer surface. However, as long as the buffer solution chambers 103 and 104 have a shape in which a liquid can be held, its shape is not especially limited.

As long as the separation part housings 108 and 109 hold a separation part stacked body 129, and have a structure in which the ends 112 and 113 of the transfer electrodes 110 and 111 are exposed, any separation part housings can be used. In addition, in this embodiment, the ends 112 and 113 are alternately exposed. However, the present invention is not limited to the above, and the ends 112 and 113 may be exposed on one side.

Figure 3:
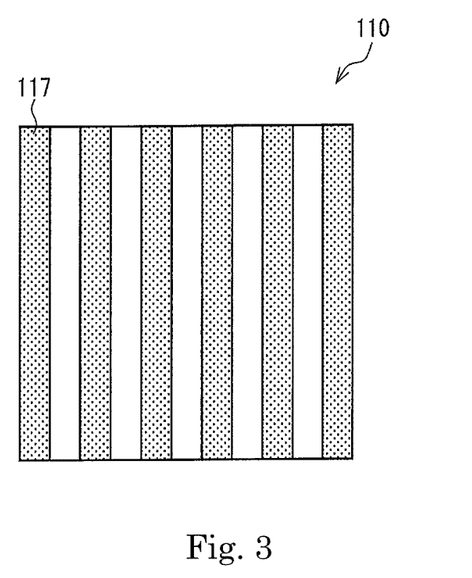
FIG. 3 is schematic diagram showing a structure of a transfer electrode of a biological molecule separation apparatus related to one embodiment of the present invention.

Here, as described later, the transfer electrodes 110 and 111 have a unique structure as shown in FIG. 3. A simple wire connection method can not electrically connect a transfer electrode with a power source, the simple wire connection method used in a transfer apparatus using a flat plate type electrode used in a conventional technology.

However, in the biological molecule separation apparatus 100 of this embodiment, end parts 112 and 113 are exposed, thereby the power source 106 can be easily electrically connected with the transfer electrodes 110 and 111. The embodiment is not limited to the following, however an end of a conducting line from the power source 106 is provided with a jig made of a conducting body, the jig being able to contact with the entire end part. This jig is respectively contacted with the end parts 112 and 113. When the jig is contacted with the entire end part, the jig is contacted with all of line shaped conducting bodies 117 of the transfer electrode shown in FIG. 3. Thereby, the transfer electrode can be easily electrically connected with the power source. In addition, the end part 112 is an upper end or a bottom end in the figure.

In addition, the end parts 112 and 113 may be exposed toward one direction. However, as in the biological molecule separation apparatus 100 of this embodiment, if the end parts 112 and 113 are exposed respectively toward opposing directions, when connection at one end part is performed, it is not necessary to consider contact with the other end part, thus this embodiment is further preferable.

In addition, the reason why the end parts 112 and 113 are exposed is, as mentioned above, for the purpose that the power source 106 is electrically connected with the transfer electrodes 110 and 111. If, in other embodiments, the power source 106 can be electrically connected with the transfer electrodes 110 and 111, the end parts 112 and 113 may not be exposed. In such a case, for example, an electric wire may be arranged inside the separation part housings 108 and 109 so that the power source 106 is electrically connected with the transfer electrodes 110 and 111. A well known circuit technology such as a switch mechanism can be used for switching the connection.

The buffer solution chambers 103 and 104, and, the separation part housings 108 and 109 may be formed as one body, or may be comprised of several assembled components. In this embodiment, at least, the separation part housings 108 and 109 are comprised of different components, and are used after assembling them. In this case, after the separation part stacked body 129 is manufactured at another place it is easy to assemble the body 129 inside the biological molecule separation apparatus 100.

In addition, after the biological molecule separation apparatus 100 is used, when the biological molecule adsorption film 122 is recovered, if the separation part housings 108 and 109 have a structure in which the housings 108 and 109 can be easily peeled from each other, recovering the biological molecule adsorption film 122 can be easily and preferably performed. In this embodiment, the separation part housings 108 and 109, and the buffer solution chambers 103 and 104 are constituted such that the above components are divided up among the separation part housings 108 and 109. A groove 114 is formed at a connecting part thereof. Therefore, when a paddle or the like is inserted into the groove 114, the separation part housings 108 and 109 are easily peeled from each other. Thereby, the biological molecule adsorption film 122 can be recovered.

As long as the separation electrodes 101 and 102 are made of a conductive material, any separation electrode can be used. For example, if a simple apparatus is desired, a simple wire or the like can be used. Electrical connection between the power source and the separation electrodes 101 and 102 can be performed by a well known technology. For example, if a simple method is desired, a clip or the like can be used. In addition, the separation electrode 101 is used as an anode, and the separation electrode 102 is used as a cathode. The reason why the above embodiment is adopted is as follows. A biological molecule having a minus charge is separated from a side for introducing a sample including the biological molecule of the biological molecule separation medium 125 to other side. The direction of the electrode is not especially limited.

A general power source can be used for the power source 106. It is preferable that the power source 106 has a constant-voltage circuit or a constant current circuit.

As described below, the transfer electrodes 110 and 111 can be formed on any substrate. In one embodiment, the transfer electrodes 110 and 111 may be formed directly on the separation part housings 108 and 109. In this embodiment, the number of components of the biological molecule separation apparatus 100 is reduced, and a manufacturing process thereof can be simplified.

Figure 2:
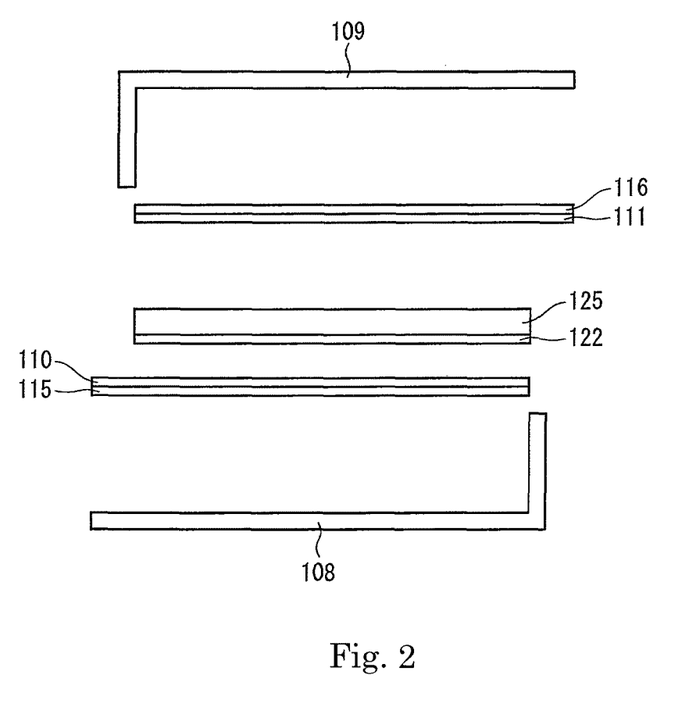
FIG. 2 is a schematic diagram showing a structure of a transfer electrode of a biological molecule separation apparatus related to one embodiment of the present invention.

In addition, in one embodiment, as shown in FIG. 2, the transfer electrode 110 may be formed on a substrate 115 which is different from the separation part housing 108, and the transfer electrode 111 may be formed on a substrate 116 which is different from the separation part housing 109. In assembling a biological molecule separation apparatus 100, the separation part housing 108 is combined with the substrate 115, and the separation part housing 109 is combined with the substrate 116.

A physical method using an authorized tally or the like, or a chemical method using an adhesive can be used to assemble the substrate 115 or 116 and the separation part housing 108 or 109. If separation part housings 108 and 109, and transfer electrodes 110 and 111 are respectively manufactured, a biological molecule separation structure body 107 can be assembled by selecting transfer electrodes 110 and 111 of various types (described in detail below) depending on the intended use.

Next, a structure of the transfer electrodes 110 and 111 is explained in detail. Transfer electrodes 110 and 111 have a structure in which a plurality of line shaped conductors 117 extend towards a third direction, the third direction being perpendicular to the first direction which is defined by the buffer solution chambers 103 and 104, and the third direction being perpendicular to the second direction which is a stacking direction of the separation part stacking body 129. In the structure, the plurality of line shaped conductors 117 are arranged along the first direction. FIG. 3 is a schematic drawing of a structure of the transfer electrode 110. The transfer electrodes 110 and 111 may be called a stripe electrode because of its shape.

Here, the transfer electrodes 110 and 111 are not generally used flat plate type electrodes but are stripe electrodes. Its effect is explained below.

Figure 4A:
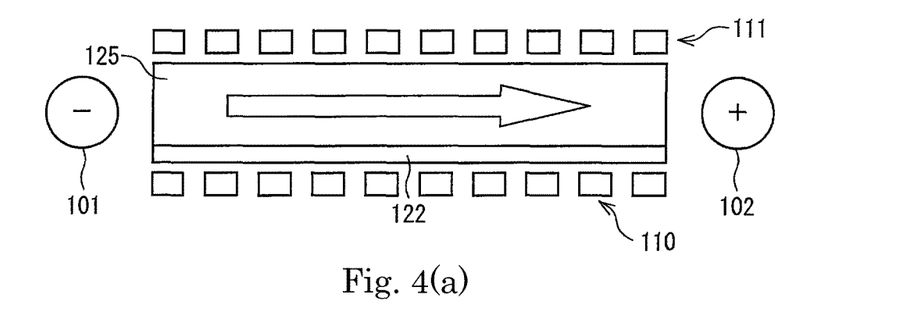
FIG. 4(a) is a schematic diagram explaining an operation during a separation process in a biological molecule separation apparatus related to one embodiment of the present invention.
Figure 4B:
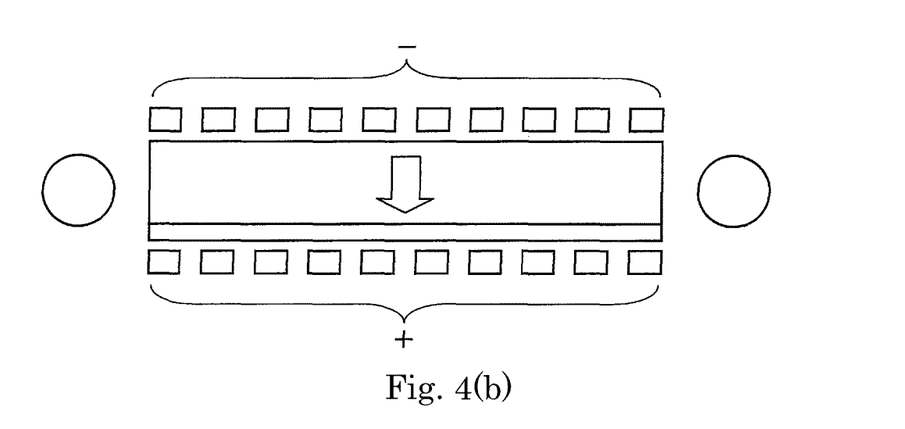
FIG. 4(b) is a schematic diagram explaining an operation during a transfer process in a biological molecule separation apparatus related to one embodiment of the present invention.

FIG. 4 is a schematic diagram explaining an operation in a biological molecule separation apparatus 100. FIG. 4(a) explains an operation in a separation process. FIG. 4(b) explains an operation in a transfer process.

As shown in FIG. 4(a), in the separation process, the separation electrode 101 has a minus potential, and the separation electrode 102 has a plus potential. Therefore, a biological molecule inside the biological molecule separation medium 125 moves in the first direction (a direction shown by an arrow in the figure) which is from the separation electrode 101 toward the separation electrode 102. At this time, because the transfer electrodes 110 and 111 are comprised of the line shaped conductor 117 in the third direction perpendicular to the first direction, a potential is constant along the third direction without influencing the gradient of a potential along the first direction. Therefore, the transfer electrodes 110 and 111 do not prevent the biological molecule from moving. On the other hand, in the case where a flat plate type electrode is arranged at a position of the transfer electrodes 110 and 111, a potential is constant along the first direction, thereby the biological molecule does not move.

That is, the transfer electrodes 110 and 111 are arranged so that a direction from the transfer electrode 110 toward the transfer electrode 111 is perpendicular to a direction in which a voltage is applied. The transfer electrodes 110 and 111 are insulated from each other, and have the plurality of conductors which are arranged along the direction in which the voltage is applied. Therefore, a potential in a direction in which a voltage is applied does not become uniform, and a biological molecule inside the biological molecule separation medium 125 can be well separated.

Then, as shown in FIG. 4(b), in the transfer process, the separation electrodes 101 and 102 do not apply a voltage to the biological molecule separation medium 125 while the transfer electrode 110 has a plus potential and the transfer electrode 111 has a minus potential. Therefore, a biological molecule inside the biological molecule separation medium 125 moves in the second direction (which is a direction from the transfer electrode 111 toward the transfer electrode 110) in which the biological molecule adsorption film 122 is arranged. In this way, the biological molecule is separated, and is transferred to the biological molecule adsorption film 122.

The transfer electrodes 110 and 111 can be made of a conductive material. In this embodiment, platinum is used. However, the material is not limited to platinum. Other metals such as gold can be used. The transfer electrodes 110 and 111 can have the above mentioned structure. A method for manufacturing the transfer electrodes is not especially limited. However, as described below, the transfer electrodes can be manufactured as follows. A substrate which is used to form the transfer electrodes 110 and 111, the substrate being the separating part housings 108 and 109, or, the substrate 115 and 116, is prepared. A film of a conducting material is formed on the substrate. Thereafter, a laser engraving machine or the like cuts a groove. Thereby, the plurality of line shaped conductors 117 which are arranged along a specific direction can be formed. An insulator such as a resin and a glass can be used for the substrate.

In the case where a resin is used for the substrate, a porous substrate is preferably made by a stretching method, a pore-forming method or the like. In this case, a resin used as the substrate also preferably functions as porous films 120 and 121 which are described below. A synthetic resin of a (meth) acrylic resin, a fluorinated resin or the like can be preferably used for the resin.

In addition, in another embodiment, in order to manufacture the transfer electrodes 110 and 111, as shown in FIG. 3, a conductive material can be formed on the substrate as a line by a printing technology such as an ink jet technology. In this case, a resin film or the like as well as a glass substrate can be used as the substrate. According to this method, the transfer electrodes 110 and 111 can be more easily manufactured.

In addition, further, in another embodiment, the transfer electrodes 110 and 111 can be formed by a method in which a conductive fiber is knitted into paper such as a paper filter by a well known knitting technology so that the conductive fiber is arranged in a specific direction. In this case, a paper filter used as a substrate preferably functions as porous films 120 and 121 which are described below.

Porous films 120 and 121 are not limited as long as the porous films 120 and 121 are made of a porous material. For example, an easy way is to use a general paper filter. In addition, for example, a synthetic resin, a rubber, a ceramic or the like can be used. A thickness thereof is not especially limited. However, typically, the thickness can be 10-300 μm.

Since porous films 120 and 121 are porous, a buffer solution 160 penetrates to the porous films 120 and 121. Here, the porous films 120 and 121 are exposed on the buffer solution chambers 103 and 104. Therefore, a buffer solution penetrates the porous films 120 and 121 in the separation process and the transfer process. Therefore, the porous films 120 and 121 can supply the biological molecule separation medium 125 with the buffer solution 160, the biological separation medium 125 being preferably wet.

In addition, since the porous films 120 and 121 are porous, the porous films 120 and 121 can include bubbles. During the transfer process, at the transfer electrodes 110 and 111, electrolysis of water occurs, thereby oxygen is generated at an anode and hydrogen is generated at a cathode. In the case where the bubbles generated in this way enter between the biological molecule separation medium 125 and the biological molecule adsorption film 122, or, in the case where the bubbles enter inside the biological molecule separation medium, a transfer pattern of the biological molecule from the biological molecule separation medium 125 toward the biological molecule adsorption film 122 is badly influenced. The porous films 120 and 121 adsorb the bubbles thereby the bad influence can be prevented.

In addition, bubbles generated from the transfer electrodes 110 and 111 are oxygen and hydrogen generated by electrolysis of water. Therefore, the amount of bubbles generated at a cathode is twice as large as the amount of bubbles generated at an anode. Then, in this embodiment, the transfer electrode 110 is an anode and the transfer electrode 111 is a cathode. Therefore, it is designed so that the thickness of the porous film 121 in a side of the transfer electrode 111 is twice as large as the thickness of the porous film 120 in a side of the transfer electrode 110. In this design, the bubbles can be preferably removed.

The biological molecule adsorption film 122 may be called a transfer film, and is used for transferring a biological molecule inside the biological molecule separation medium 125 (an electrophoresis gel) while a separation pattern of the biological molecule is maintained. A material or the like used for the biological molecule adsorption film 122 is not especially limited, and can be a material generally used in the art. For example, such a material is a nitrate film, an ester in which cellulose is mixed, a cellulose acetate film, a polyvinylidene fluoride film, a nylon film, a polyolefin film or the like.

A peeling film is sandwiched between the biological molecule separation medium 125 and the biological molecule adsorption film 122, therefore the biological molecule separation medium 125 is easily peeled from the biological molecule adsorption film 122. The peeling film 123 is not especially limited as long as a biological molecule separated during a separation process passes through a peeling film from the biological molecule separation medium 125 to the biological molecule adsorption film 122 while the separation pattern is maintained. However, a peeling film is preferably porous. More preferably, it is a porous thin film having homogeneous pores. Such a porous thin film is, for example, a porous film of which the main component is polycarbonate, polyether sulfone, polyolefin or the like. These films do not prevent a biological molecule separation medium 125 from polymerizing and do not prevent separation and transfer due to electrophoresis of a biological molecule. In addition, a commercially available film which is generally used as a filtration film may be used as the peeling film 123.

A biological molecule separation medium 125 is not especially limited as long as the biological molecule separation medium 125 is a carrier having a molecular sieving effect. However, it is preferable that a gel which is generally used for electrophoresis is used. For example, a gel using a gelation agent such as polyacrylamide and agarose can be preferably used. In this embodiment, the biological molecule separation medium 125 is comprised of a first step separation medium 126 and a second step separation medium 127.

The first step separation medium 126 may be generally called a condensation gel and a concentration of a gelation agent of the first step separation medium 126 is lower than that of the second step separation medium 127. As mentioned above, a purpose of the first step separation medium 126 is to condense a biological molecule or a sample including a biological molecule. Separation of a biological molecule is actually performed at the second step separation medium 127. Therefore, a biological molecule separation medium 125 may be comprised of only the second step separation medium 127.

Figure 5:
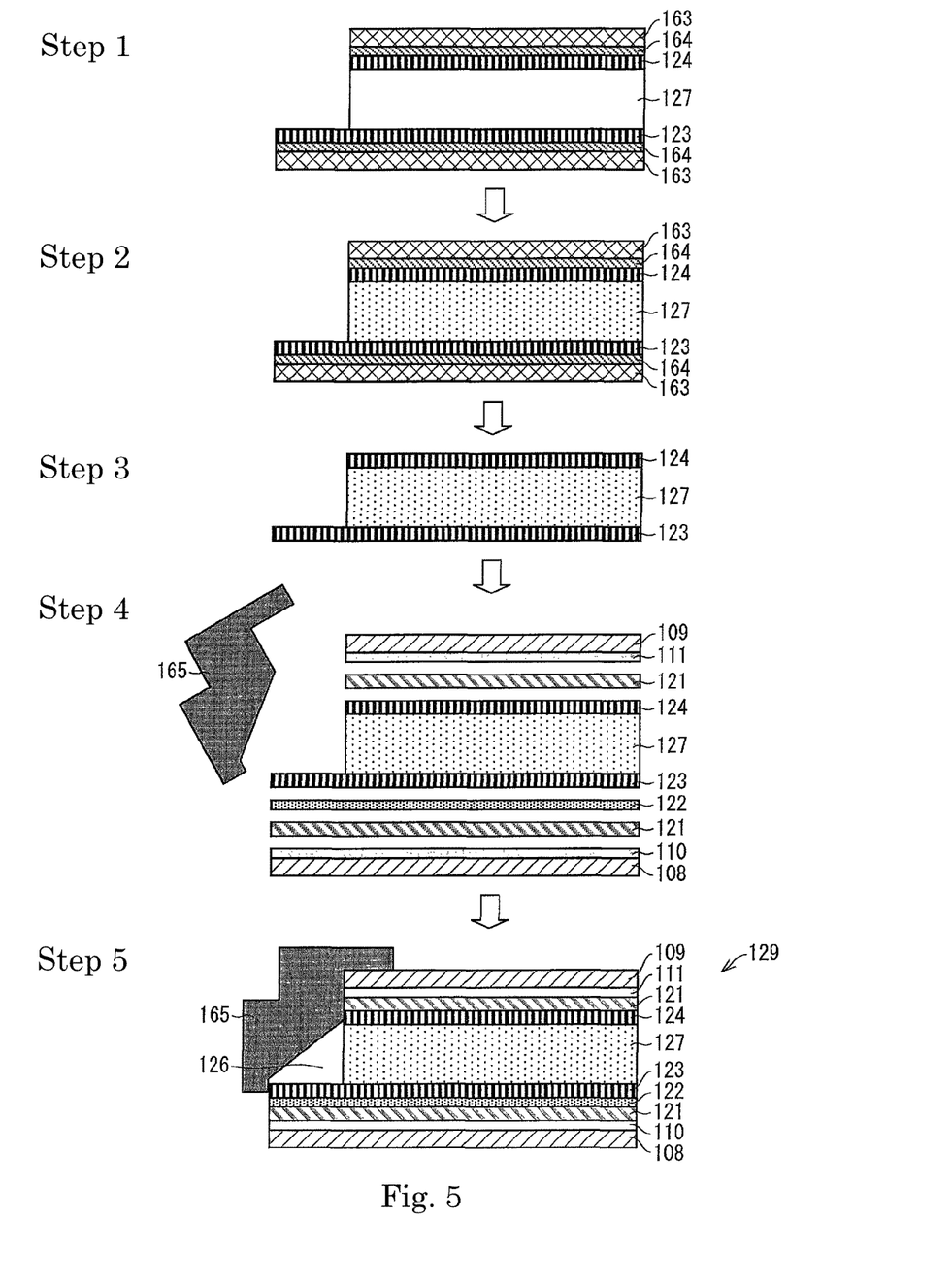
FIG. 5 is a diagram explaining one example of a method for manufacturing a biological molecule separation apparatus related to one embodiment of the present invention.

As mentioned above, a general gel can be used as a biological molecule separation medium 125. In this case, as shown in FIG. 5, in this embodiment, polymerization of a gel as a biological molecule separation medium 125 is performed at a place different from a biological molecule separation apparatus 100, however polymerization may be performed directly inside a biological molecule separation medium 100. Hereinafter, an example of a method for manufacturing a biological molecule separation medium 125 in this embodiment is explained using FIG. 5. In addition, the following explanation shows only an example, and the present invention is not limited to the following explanation. Other methods can be used as long as a biological molecule separation apparatus 100 having the above structure can be manufactured.

Firstly, a temporal gel chip 163 has a cavity corresponding to a desirable shape as a biological molecule separation medium 125, the cavity being inside the chip 163. An appropriate adhesive material 164 is applied to the inside of the chip 163, thereafter peeling films 123 and 124 are attached to the chip, and are dried at 50-80 degrees Celsius. (step 1) In addition, a purpose of this step is to manufacture a gel with a highly accurate shape. Therefore, it is possible to omit this step. A PVA or the like can be used as an adhesive material 164.

Next, a liquid second step separation medium 127 is injected into the temporal gel chip 153. (step 2)

When the medium 127 becomes a gel, the gel is taken out of the temporal gel chip 163. (step 3)

A biological molecule separation structure body 107 is assembled. (step 4) Firstly, a biological molecule adsorption film 122 is arranged under the biological molecule separation medium 127 sandwiched between peeling films 123 and 124. Further the biological adsorption film 122 with the medium 127 having the films 123 and 124 is sandwiched between porous films 120 and 121. A stacked body 129 obtained in this way is sandwiched between separation part housings 108 and 109 having transfer electrodes 110 and 111. Further the separation part housings 108 and 109 are assembled using an adhesive. At this time, in order to form a first step separation medium 126, a cover 165 for forming a cavity corresponding to the first step separation medium 126 is attached to the biological molecule separation structure body 107.

The cavity formed by the cover 165 is filled with a liquid first step separation medium 126, and the liquid becomes a gel. (step 5) In one embodiment, in the case where a pore 128 is formed at a first step separation medium 126, the cover 165 can be formed with a projection part corresponding to the pore 128. In this way, a biological molecule separation medium 125 can be formed. In addition, before the medium 125 is used, the cover 165 is removed.

A buffer solution 160 can be an electrolyte. A buffer solution having a composition which is generally used for electrophoresis or transfer may be used.

A biological molecule to be separated is not limited as long as the molecule is a substance to be separated or analyzed by electrophoresis or transfer. For example, it can be polypeptide or polynucleotide. As a sample including a biological molecule, a prepared material from a biological material (for example, bion, biological fluid, cell line, tissue culture material, or a piece of tissue) can be preferably used. In addition, the above biological molecule can be labeled by a fluorescent material, a radio isotope or the like.

The present invention is not limited to the above respective embodiments, and can be variously changed within a range showed by the claims. Embodiments which are obtained by appropriately combining technological means respectively disclosed in different embodiments are also included in a technological range of the present invention.

In addition, all academic documents and patent documents described in this specification are incorporated herein by reference. According to a biological molecule separation apparatus related to the present invention, even if first and second transfer electrodes are arranged in the apparatus, the first and second transfer electrodes do not influence application of a voltage by first and second separation electrodes. Therefore, separation and transfer of a biological molecule can be continuously performed just by operating the state of a current flowing in a separation electrode and a transfer electrode. Thereby, a practical biological molecule separation apparatus in which both electrophoresis and transfer can be performed by a simple operation can be provided.

EXAMPLE

A biological molecule separation apparatus 100 was manufactured and was used. The details are described below.
[Manufacturing a Transfer Electrode]
A plate (6.5 cm×5 cm×3 mm) of polymethylmethacrylate (PMMA) was prepared for manufacturing a transfer electrode 110 and a plate (6.5 cm×4.8 cm×3 mm) of polymethylmethacrylate (PMMA) was prepared for manufacturing a transfer electrode 111 (substrates 115 and 116). A binder of Cr was deposited on one surface of the plate using a sputtering apparatus. Further, Pt of about 2000 angstrom was deposited thereon.
The Pt was manufactured with a stripe shape using a $CO_2$ laser engraver. A line width of Pt was 100 μm and a space between lines was 100 μm in the transfer electrodes 110 and 111.
[Manufacturing a Housing of a Biological Molecule Separation Structure (Chip) 107]
A separation part housing 108 was manufactured using polymethylmethacrylate, the housing 108 storing the substrate 115 with the transfer electrode 110 while one end 112 of the substrate 115 was exposed to the outside. The exposed end part 112 is one side of an end part along a direction of the Pt line. A width of the end part 112 was 3 mm. In addition, similarly, a separation part housing 109 was manufactured using polymethylmethacrylate, the housing 109 storing the substrate 116 with the transfer electrode 111 while one end 113 of the substrate 116 was exposed to the outside. In addition, the separation part housing 108 and 109 were overlapped and attached to each other so that a solution tank for receiving an electrophoresis buffer could be formed.
[A Biological Molecule Adsorption Film (a Transfer Film) 122]
PORAFIL MV (a product of HEREY-NAGEL) which is an ester film mixed with cellulose was used as a biological molecule adsorption film 122.
[Manufacturing a Biological Molecule Separation Structure (Chip) 107]
The substrate 115 or 116 arranged with the transfer electrode 110 or 111 is attached to the separation part housings 108 and 109 respectively. A filter paper of 115 μm thickness (Hardened Low Ashless Quantitative filter paper No. 50, a product of WHATMAN) as a porous film 120 was arranged on the transfer electrode 110. Two pieces of filter papers of 115 μm thickness (Hardened Low Ashless Quantitative filter paper No. 50, a product of WHATMAN) as porous films 121 were arranged on the transfer electrode 111.
A biological molecule adsorption film 122 having a size of 5 cm×6 cm was immersed in distilled water and thereafter was arranged, thereby excess water was removed from the film 122 by the filter paper so that the film 112 did not dry. Thereafter, a polycarbonate film of 20 μm thickness (ISO-PORE, a product of Millipore) as peeling films 123 and 124 were arranged. Then, the separation part housing 109 was attached to the separation part housing 108 using a UV curable adhesive.

Figure 6:
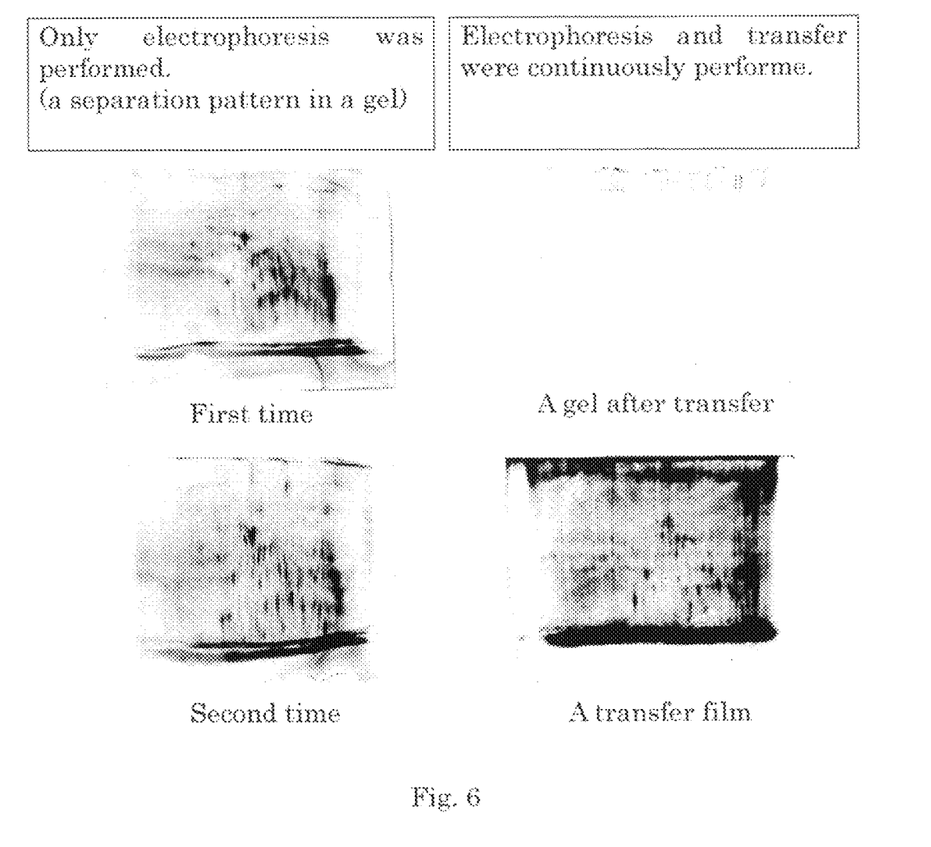
FIG. 6 is a photograph showing a result after using a biological molecule separation apparatus related to one embodiment of the present invention.

A lower end part (a part contacting with a buffer solution tank 104) of a region for forming a supporting body for electrophoresis (a cavity formed by the separation part housings 108 and 109) was sealed. Thereafter, a polyacrylamide gel solution which was a material for a biological molecule separation medium 125 was injected from an upper part (a part contacting with a buffer solution tank 103). After leaving for a certain period, the gel was polymerized, thereby a biological molecule separation medium 125 (a second step separation medium 127) was formed.
The polyacrylamide gel including 13% of acrylamide, 375 mM of Tris-HCL (pH 8.8), 0.1% of ammonium persulfate, 0.1% of N,N,N',N' tetramethylethylenediamine was used. In particular, a mixed solution of 29.2% of acrylamide-0.8% of methylenebisacrylamide was added so that a final concentration of acrylamide included in polyacrylamide gel became 13%. A condensation gel (a first step separation medium 126) of which the final concentration of acrylamide was 3%, was formed.
[A Sample Including a Biological Molecule]
A water-soluble protein fraction of a mouse liver labeled by a fluorochrome Cy5 was used as a sample.
[Separation Process]
Two dimensions electrophoresis was performed by using the biological molecule separation structure 107, thereby a biological molecule was separated based on charge and molecular weight of a protein material.
One dimension isoelectric point electrophoresis was performed according to a usual method under the following conditions. (200 V, 5 minutes); (200-1000 V, 5 minutes); (1000 V, 5 minutes); (1000-6000 V, 10 minutes); and (6000 V, 20 minutes). The total time was 45 minutes.
An anode buffer including 25 mM of tris, 192 mM of glycine and 0.1% of SDS; and a cathode buffer including 150 mM of Tris-HCL (pH 8.8) were used as buffer solutions (two dimension electrophoresis buffer) 160. 5 ml of the above buffers were respectively added to the buffer solution tanks 103 and 104 of the biological molecule separation structure 107. A gel in which a biological molecule was separated by isoelectric point electrophoresis was connected to a first step separation medium (a condensation gel) 126, and electrophoresis under a condition of a constant current of 20 mA was performed for 30 minutes.
[Transfer Process]
After the separation process (electrophoresis) was completed, a biological molecule which was developed at the biological molecule separation medium 125 (a electrophoresis gel) was transferred to an ester film in which cellulose was mixed (a biological molecule adsorption film 122).
Two exposed parts (end parts 112 and 113) of the transfer electrodes 110 and 111 were electrically connected to a power source 106 by a jig in which an aluminum film was attached to a silicone rubber. A voltage was applied and thereby a biological molecule was transferred from a biological molecule separation medium 125 to a biological molecule adsorption film 122. The condition under which a voltage was applied changed in the following order. (1V, 10 minutes), (2V, 10 minutes), (5V, 40 minutes)
[Detection]
A protein material was detected by detecting fluorescence of Cy5 using a scanner (Typhoon Trio, a product of GE Healthcare).
[Result]
FIG. 6 shows a detection spot of a protein material on a transfer film when transfer in addition to electrophoresis was performed by the biological molecule separation apparatus 100 related to the present invention. As comparison examples, a detection spot of a protein material in a gel (first time, second time) in the case where only electrophoresis was performed in two tests was shown. As shown in FIG. 6, both spots are similar to each other when a detection spot of a protein material in a gel in the case where only electrophoresis was performed was compared with a detection spot of a protein material on a transfer film in the case where transfer in addition to electrophoresis was performed. From this result, it was confirmed that electrophoresis and transfer can be continuously performed inside the apparatus (chip).

Industrial Applicability

The present invention can be used in the field of manufacturing an apparatus for analyzing a biological molecule, in medical services, research, education or the like.

What is claimed is:

1. A biological molecule separation apparatus, comprising:
a first separation electrode;
a second separation electrode;
a first buffer solution chamber, the first separation electrode arranged in the first buffer solution chamber, and the first buffer solution chamber receiving a buffer solution;
a second buffer solution chamber, the second separation electrode arranged in the second buffer solution chamber, and the second buffer solution chamber receiving a buffer solution;
a biological molecule separation medium, one end of the biological molecule separation medium exposed on the first buffer solution chamber, and the other end of the biological molecule separation medium exposed on the second buffer solution chamber;
a biological molecule adsorption film;
a first transfer electrode comprising a first plurality of line-shaped conductors extending in a direction perpendicular to a first direction, the first direction defined by the first buffer solution chamber and the second buffer solution chamber, the first plurality of line-shaped conductors being arranged in the first direction;
a second transfer electrode comprising a second plurality of line-shaped conductors extending in a direction perpendicular to the first direction, the second plurality of line-shaped conductors being arranged in the first direction; and,
a holding part which holds the first transfer electrode, the biological molecule adsorption film, the biological molecule separation medium and the second transfer electrode, wherein the first transfer electrode, the biological molecule adsorption film, the biological molecule separation medium and the second transfer electrode are stacked in this order.

2. The apparatus according to claim 1, further comprising:
a first substrate on which the first transfer electrode is arranged; and
a second substrate on which the second transfer electrode is arranged, wherein
the holding part holds the first substrate and the second substrate.

3. The apparatus according to claim 2, wherein the first substrate and the second substrate are made of a resin or a paper.

4. The apparatus according to claim 1, wherein the first transfer electrode and the second transfer electrode are formed on the holding part.

5. The apparatus according to claim 1, wherein one end of the first transfer electrode and one end of the second transfer electrode are exposed on the holding part, and the one end of the second transfer electrode is opposite to the one end of the first transfer electrode.

6. The apparatus according to claim 1, further comprising:
a first porous film arranged between the first transfer electrode and the biological molecule adsorption film and a second porous film arranged between the biological molecule separation medium and the second transfer electrode; wherein
one side of the first porous film is exposed on the first buffer solution chamber and the other side of the first porous film is exposed on the second buffer solution chamber, and
one side of the second porous film is exposed on the first buffer solution chamber and the other side of the second porous film is exposed on the second buffer solution chamber.

* * * * *